US008583410B2

(12) United States Patent
Sisk et al.

(10) Patent No.: US 8,583,410 B2
(45) Date of Patent: Nov. 12, 2013

(54) METHOD FOR OBTAINING CONSISTENT AND INTEGRATED PHYSICAL PROPERTIES OF POROUS MEDIA

(75) Inventors: Carl D. Sisk, Houston, TX (US); Theodore E. Zaleski, Jr., Spring, TX (US)

(73) Assignee: Ingrain, Inc., Houston, TX (US)

( * ) Notice: Subject to any disclaimer, the term of this patent is extended or adjusted under 35 U.S.C. 154(b) by 581 days.

(21) Appl. No.: 12/790,066

(22) Filed: May 28, 2010

(65) Prior Publication Data

US 2011/0295580 A1     Dec. 1, 2011

(51) Int. Cl.
    G06G 7/48      (2006.01)
    G01V 1/40      (2006.01)
    G01V 3/18      (2006.01)
    G01V 5/04      (2006.01)
    G01V 9/00      (2006.01)

(52) U.S. Cl.
    USPC .................................... 703/10; 702/6

(58) Field of Classification Search
    USPC .................... 703/10; 706/13; 702/6
    See application file for complete search history.

(56) References Cited

U.S. PATENT DOCUMENTS

| 6,516,080 | B1* | 2/2003 | Nur ................................. 382/109 |
| 6,941,255 | B2 | 9/2005 | Kennon et al. |
| 2004/0204857 | A1* | 10/2004 | Ramamoorthy et al. ......... 702/7 |
| 2010/0128932 | A1* | 5/2010 | Dvorkin et al. ............... 382/109 |
| 2010/0131204 | A1 | 5/2010 | Dvorkin et al. |
| 2010/0299125 | A1* | 11/2010 | Ding et al. ....................... 703/10 |

FOREIGN PATENT DOCUMENTS

WO    2005108965 A1    11/2005

OTHER PUBLICATIONS

Arns, Christoph H. et al., "Computation of Linear Elastic Properties from Microtomographic Images: Methodology and Agreement Between Theory and Experiment", Sep.-Oct. 2002, National Institute of Standards and Technology (NIST).*
Camargo, Edgar et al., "Nodal Analysis-Based Design for Improving Gas Lift Wells Production", Apr. 15, 2008, WSEAS Transactions on Information Science and Applications, Issue 5, vol. 5.*
Bennion, D.B. et al., Recent Advances in Laboratory Test Protocols to Evaluate Optimum Drilling, Completion and Stimulation Practices for Low Permeability Gas Reservoirs, 2000, Society of Petroleum Engineers Inc.*
Schietz, Michael, "Optimization of Well Start-Up", Aug. 28, 2009, Master of Science Thesis, Department of Petroleum Production and Processing, University of Leoben.*
Notification of Transmittal of the International Search Report and the Written Opinion of the International Searching Authority issued in corresponding International Patent Application No. PCT/US2011/037500 dated Feb. 9, 2012 (8 pages).

(Continued)

Primary Examiner — David Silver
Assistant Examiner — Cedric D Johnson
(74) Attorney, Agent, or Firm — Kilyk & Bowersox, P.L.L.C.

(57) ABSTRACT

A method and system for obtaining a consistent and integrated set of physical properties of a sample specimen of porous media, e.g., rock, in which a specimen is prepared for imaging. The specimen is imaged multiple times to yield a set of images that undergo a segmentation process to provide a digital representation of the sample specimen. The digital representation provides a view of the solid phase and pore space of the sample specimen. The digital representation may be used to determine a plurality of physical properties of the sample porous specimen, such that the sample porous specimen may remain intact throughout the method.

20 Claims, 4 Drawing Sheets

(56) References Cited

OTHER PUBLICATIONS

Youssef et al., "High Resolution CT and Pore-Network Models to Assess Petrophysical Properties of Homogeneous and Heterogeneous Carbonates," Society of Petroleum Engineers/EAGE Reservoir Characterization and Simulation Conference, SPE No. 111427, Oct. 29, 2007, pp. 1-12 (12 pages).

Knackstedt et al., "Digital Core Laboratory: Properties of reservoir core derived from 3D images," Society of Petroleum Engineers Asia Pacific Conference on Integrated Modelling for Asset Management, SPE No. 87009, Mar. 29, 2004, pp. 1-14 (14 pages).

Adams et al., "Seeded Region Growing," IEEE Transactions on Pattern Analysis and Machine Intelligence, vol. 16, No. 6, Jun. 1994, pp. 641-647 (7 pages).

Sakellariou et al., " Developing a Virtual Materials Laboratory," Materials Today, vol. 10, No. 12, Dec. 2007, pp. 44-51 (8 pages).

Sandberg, "Methods for Image Segmentation in Cellular Tomography," Methods in Cell Biology, vol. 79, Jan. 1, 2007, pp. 769-798 (32 pages).

Parker, "Gray Level Thresholding in Badly Illuminated Images," IEEE Transactions on Pattern Analysis and Machine Intelligence, vol. 13, No. 8, Aug. 1, 1991, pp. 813-819 (7 pages).

Oh et al., "Image Thresholding by Indicator Kriging," IEEE Transactions on Pattern Analysis and Machine Intelligence, vol. 21, No. 7, Jul. 1999, pp. 590-602 (13 pages).

Bugani et al., "Investigating morphological changes in treated vs. untreated stone building materials by x-ray micro-CT," Anal. Bioanal. Chem., No. 391, 2008, pp. 1343-1350 (8 pages).

Felipussi et al., "Measuring Statistical Geometric Properties of Tomographic Images of Soils," IEEE Transactions on Instrumentation and Measurement, vol. 57, No. 11, Nov. 2008 (12 pages).

Gallucci et al., "3D experimental investigation of the microstructure of cement pastes using synchrotron X-ray microtomography (mu-CT)," Cement and Concrete Research, No. 37, 2007, pp. 360-368 (10 pages).

De Graef et al., "A sensitivity study for the visualisation of bacterial weathering of concrete and stone with computerized X-ray microtomography," Science of the Total Environment, No. 341, 2005, pp. 173-183 (12 pages).

Jones et al., "Characterization of methane hydrate host sediments using synchrotron-computed microtomography (CMT)," Journal of Petroleum Science and Engineering, No. 56, 2007, pp. 135-145 (10 pages).

Arns et al., "Computation of linear elastic properties from microtomographic images: Methodology and agreement between theory and experiment," Geophysics, vol. 67, No. 5, Sep.-Oct. 2002, pp. 1396-1405 (10 pages).

Auzerais et al., "Transport in sandstone: A study based on three dimensional microtomography," Geophysical Research Letters, vol. 23, No. 7, Apr. 1, 1996, pp. 705-708 (4 pages).

Fredrich et al., "Predicting macroscopic transport properties using microscopic image data," Journal of Geophysical Research, vol. 111, 2006, B03201, pp. 1-14 (14 pages).

\* cited by examiner

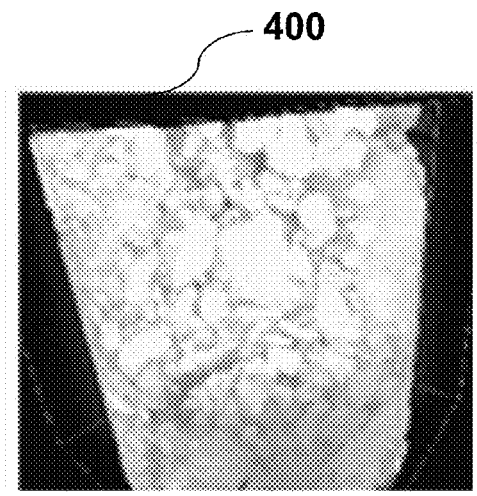 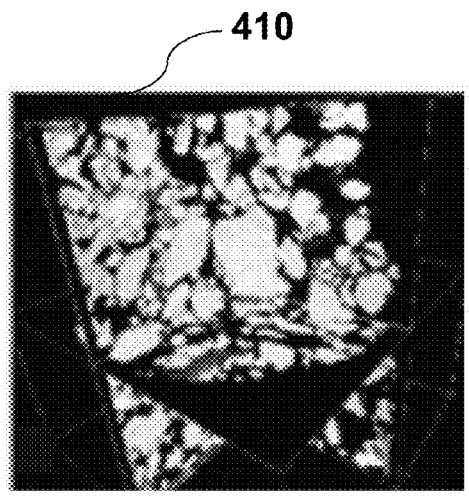
Figure 4A     Figure 4B
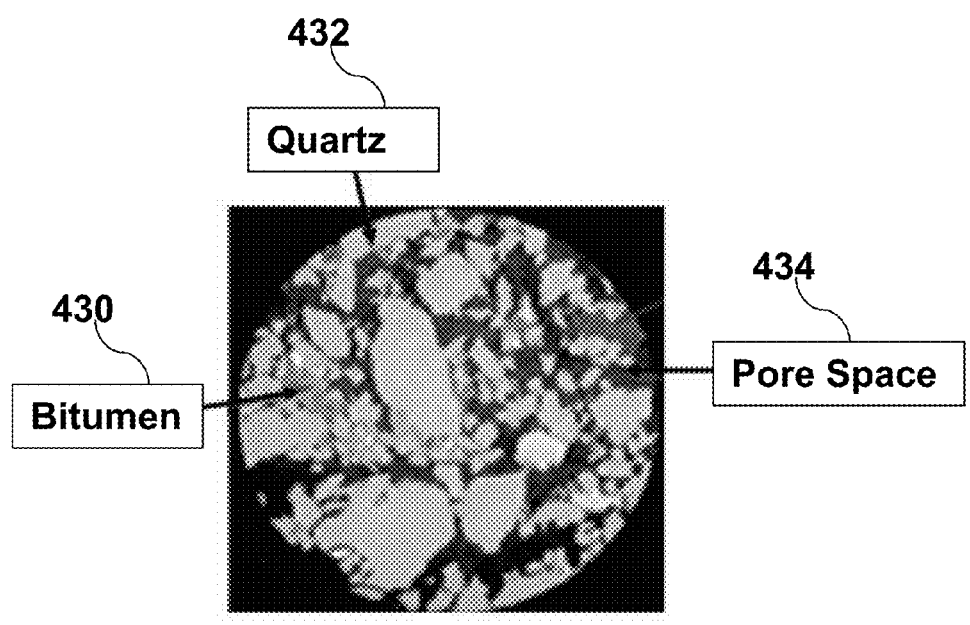
Figure 4C

METHOD FOR OBTAINING CONSISTENT AND INTEGRATED PHYSICAL PROPERTIES OF POROUS MEDIA

FIELD OF THE INVENTION

The present invention relates to methods for determining physical properties of a porous media. More particularly, in certain embodiments, the present invention relates to providing physical and fluid flow properties of porous media from a consistent sample such that the sample remains intact throughout.

BACKGROUND

It is desirable for companies that drill oil and gas wells to obtain quantitative information about formations that contain hydrocarbons. This information may be useful in order to determine the amount of oil and gas in the reservoir, how much of it can be recovered, the rate of production, and ultimately whether the hydrocarbons can be developed and produced for financial gain. Quantitative rock property data can come from various measures including indirect and direct means of evaluation. Because of the different methodologies practiced through the industry to obtain quantitative rock properties, data that is generated inherently contains variables of unknown significance because multiple samples and measurement scales are used to produce the data set. The data set may include rock properties such as porosity, absolute permeability, relative permeability, and capillary pressure data, but is not limited to such properties.

Conventional indirect means for estimating rock properties exist in the art. Among other types of indirect means, almost all wells use electric logs, run in either the open hole after drilling or the casing lined well to measure certain attributes of hydrocarbon bearing formations. Several types of open hole logs may be used to measure the properties required for an effective determination. For example, a "triple combo" log measures bulk density, neutron porosity, and formation resistivity. Using known methods, those attributes may be used with mathematical correlations to derive useful parameters such as reservoir effective porosity, effective permeability, water saturation, and other properties. Additional mathematical equations may be applied to triple combo log data to estimate rock mechanical properties, such as Young's modulus, Poisson's ratio, and in-situ stress. These parameters, especially permeability and the rock mechanical properties, play a crucial role in making decisions about reservoir size, quality, and producibility.

However, there are typically limitations to measuring the properties in this manner. Each of the logging tools incorporates one or more sensors to measure a desired attribute and sometimes different logging tools are run simultaneously to reduce the time required for the surveys. Logging techniques do not require physical examination or direct inspection of the rock for the most part. For example, certain logging tools obtain images of the formation to measure a desired attribute of that formation. Another typical limitation is that the precise location of the measurement is only known relative to the estimated position of the logging tool at the time the measurement is made and the measurements taken are average values over some thickness of formation which can range from inches to feet. A rock property such as Formation Factor is used to determine water saturation from resistivity log measurements. In order to make those calculations, a resistivity measurement is obtained from the log in a region that is thought to contain 100% water and compared to other locations in the rock that appear to contain some amount of hydrocarbon in addition to connate water.

Direct methods are also available for measuring rock properties. A conventional direct method typically involves obtaining specimens of the rock to be evaluated and performing laboratory experiments on those specimens. One example of such an experiment is coring, a process by which intact rock specimens can be obtained from an oil and gas well. For example, a "whole core" is obtained by using a special drill bit that cuts a cylinder of rock over the interval of interest. The total cylinder can be on the order of four inches in diameter and hundreds of feet long. For handling purposes, the core may be cut into three foot lengths. From those lengths, short plugs of 1" to 1½" diameter are then taken for the laboratory tests. Because different laboratory tests require different sizes, shapes, and orientation of the samples relative to the original rock, several samples are typically prepared from a region of the core that appears to be similar. For example, it is useful to know both the horizontal and vertical permeabilities of a reservoir rock. To obtain these properties in the physical lab, one reservoir rock sample must be cut perpendicular to the core's axis whereas another reservoir rock sample must be cut parallel to the core's axis. Laboratory tests are then performed on the samples to yield the permeability in one direction based on the cut. However, there is no assurance that the obtained reservoir rock samples contain identical rock properties even though the samples came from the same region of the core and are visibly similar. Thus, physical laboratory analysis involved with direct methods of measuring rock properties is limited because of the scale, size, and requirement of different samples for different pieces of equipment. The results obtained from such an analysis are usually not internally consistent because the sample specimens may vary in their respective properties.

Once the sample specimen has been used to determine a property such as, for example, a horizontal or vertical permeability, that sample may not be useful for obtaining other rock properties. For example, to determine grain size distribution, yet another specimen must be obtained from the same region of the core and crushed so that a laser particle size analysis or sieve analysis can be conducted.

Similarly, as in the aforesaid example, other Special Core Analyses (SCAL) would also require their own dedicated samples that are sometimes altered or destroyed in the procedure. For example, relative permeability studies are conducted using steady state or unsteady state methods which require a flow rate to be selected for the lab test. If there is a need to determine relative permeability at a different flow rate or to change from an unsteady state to a steady state analysis, the core used for the initial analysis cannot be relied upon to be in original condition, if it is available at all. Thus, a new core sample must be used.

Similarly, capillary pressure determinations in the lab require pumping fluid into a core while monitoring pressure and flow rate. However, as in the aforementioned examples, once complete, the same core sample would not be useful for another study at a different set of flow rates and pressures.

Accordingly, it is an objective of the present invention to provide a method for obtaining a consistent and integrated set of parameters from a sample porous media. It is a further object of the invention to provide such a methodology for obtaining rock properties from a porous media from a sample such that the sample remains intact throughout the process. In particular, sample specimens of porous media can vary considerably, and there is no guarantee that the chosen rock specimens or locations all have the identical rock properties even though they came from the same region of the core and were visibly similar. Yet, the resulting data will be used as if all the samples were identical in every way. It is a further object of the invention to provide a methodology to obtain parameters for reservoir modeling from a single sample specimen by obtaining a plurality of physical properties of the single sample specimen, such that the sample specimen remains intact throughout the process.

Other information besides rock properties is needed to fully characterize oil and gas reservoirs for evaluation and predictive purposes. There are various techniques to collect reservoir fluid samples, pressure data, and information about the volumetric extent of the reservoir. Coupled with rock property data obtained from logs and cores, calculations can be made to determine where to drill wells, how to complete them, how efficiently wells are producing, and when they are depleted. Modern petroleum engineering methods use computer simulations to analyze the large volume of data that is required to do a thorough and presumably accurate analysis. The quality of the input data is critical to achieving a result that has a high probability of being correct. It is another object of the present invention to reduce the range of uncertainty of the input data from a sample porous media to improve the accuracy of the resultant output.

There is a need, therefore, for a methodology and system for providing consistent and integrated rock properties from a porous media with high accuracy to result in improved predictability of oil, gas, or reservoir well design and fluid flow characteristics. There is a further need for obtaining rock properties from a porous media such that the sample specimen may remain intact. There is a further need for performing laboratory analysis on a sample specimen that can come to stabilization sooner in the simulator and require less history matching overall.

As presently stated, these and other limitations within the current art are solved by the present invention.

SUMMARY

This invention relates to a methodology and system for a consistent and integrated determination of the physical properties and fluid characteristics of a porous media.

The methodology developed herein gives oil and gas companies a pore scale understanding of their reservoir rocks. To contrast, log and core analysis done in a physical laboratory provides quantitative information at the meter/decimeter level of resolution and there is uncertainty associated with integrating data obtained from similar but not verifiably identical sources. The methodology developed herein analyzes formation samples at the centimeter, millimeter, micron, and smaller level of resolution and rock properties are calculated on a single specimen of rock that is determined to be representative of a region of interest in a core. Thus, uncertainty is reduced and the potential for introducing variables when selecting multiple samples is eliminated.

In accordance with the present disclosure, a method is provided to obtain a consistent and integrated set of physical properties of a porous specimen for modeling a reservoir. The method comprises the steps of receiving an unprepared sample specimen of porous media, wherein the unprepared sample specimen was extracted from the Earth. The unprepared sample specimen is prepared for imaging, wherein the preparing results in a sample specimen. Next, the sample specimen is imaged to generate a three-dimensional tomographic image of the sample specimen. The tomographic image is then segmented into pixels each representing pore space or grain, such as, for example, rock grain, and the segmented image is used to perform a set of computations for the sample specimen, wherein the set of computations determines a plurality of physical properties, and wherein the sample specimen remains intact throughout the method.

In addition, a system for obtaining consistent and integrated physical properties of a porous specimen for modeling a reservoir is provided, the system comprising an unprepared sample specimen of porous media, wherein the unprepared sample specimen was extracted from the Earth, wherein the unprepared sample specimen is prepared for imaging, wherein the preparing results in a sample specimen for an image scan; a three-dimensional tomographic image, wherein the three-dimensional tomographic image is obtained by imaging the sample specimen; segmenting the sample specimen into pixels each representing pore space or grain, such as, for example, rock grain, and wherein the segmented image is used to perform a set of computations for obtaining a plurality of physical properties of the sample specimen, wherein the sample specimen remains intact throughout.

The features and advantages of the present invention will be readily apparent to those skilled in the art upon a reading of the description of the embodiments that follow.

BRIEF DESCRIPTION OF THE DRAWINGS

A more complete understanding of the present disclosure and advantages thereof may be acquired by referring to the following description taken in conjunction with the accompanying drawings, wherein:

FIG. 4A is a representation of a raw 3-D volume in accordance with the imaging of the present invention.

FIG. 4B is a representation of three axial slices of the 3-D volume.

FIG. 4C is a single 2-D slice of the segmented image with its components identified.

While the present invention is susceptible to various modifications and alternative forms, specific embodiments thereof have been shown by way of example in the figures and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION

The present invention relates to methods for determining physical properties of a porous media. More particularly, in certain embodiments, the present invention relates to providing physical and fluid flow properties of porous media from a sample such that the sample may not be damaged.

There may be several potential advantages to the methods and compositions of the present invention. One of the many potential advantages of the methods and compositions of the present invention is that they may provide, inter alia, consistent and integrated rock properties from a single sample specimen of porous media. Another potential advantage of the methods and compositions of the present invention is the improved results of reservoir mapping and development.

This technology's unique ability to determine multiple rock properties on the same piece of sampled core provides a consistent data set, regardless of whether the computations are conducted at one time or if they are recomputed at a later date using new input parameters. Companies providing goods and services for use in developing oil or gas reservoirs potentially base major business decisions on reservoir analysis. It is believed that the present invention can provide customers with a relatively enhanced data set for reservoir analysis than is available by physical experiments or indirect means.

An embodiment of the present invention utilizes a sample specimen from a reservoir of wells in an area of interest. The sample specimen may be sandstones, shales, limestones, dolomites, carbonates, tight gas sands, oil sands, and many other types.

Figure 1:
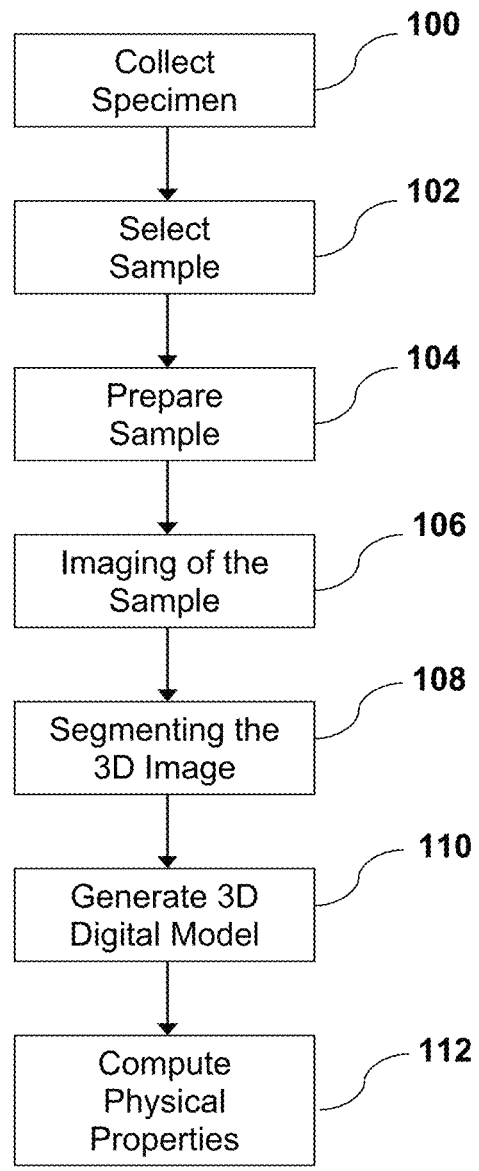
FIG. 1 is a flow chart illustrating an example method of the present invention.

FIG. 1 is a flow chart that illustrates a method of determining physical and fluid flow properties of porous media, in accordance with an embodiment of the present invention. At block 100, specimens of porous media are collected. The specimens collected may be excavated and collected from a reservoir. The types of specimens that may be collected from the Earth include sandstones, shales, limestones, dolomites, carbonates, tight gas sands, oil sands, and many other types. A sample specimen is selected for imaging at block 102. The sample specimens may be prepared for imaging.

The selected sample specimen is prepared for imaging at block 104. In an embodiment, a portion of the selected sample specimen may be used for imaging. This portion may be referenced as a "subsample." For illustrative purposes in an embodiment, a 2.5 millimeter diameter micro-core rock sample may be taken from any location in the core plug or whole core section. The selection of the subsample is performed in part by determining a region of the core sample specimen that is representative of the properties sought by the process. This technique of selecting the subsample is known as the "subsampling" technique. The subsampling technique renders the proper subsample by choosing and removing the particular portion of the sample specimen that is representative of the core region and the physical properties sought by the process. The subsample resulting from this process is the unit at which the remaining process occurs. In some instances, the subsample and the sample specimen may be the same.

A low-resolution CT scan, for example, may be conducted to map the density and assess the heterogeneity of the selected sample specimen. After CT scanning, the sample specimen may be saved for further analysis. An example of a suitable CT scanner for making images usable with methods according to the invention is sold under model designation MicroXCT Series 3D tomographic x-ray transmission microscope by Xradia, Inc., 5052 Commercial Circle, Concord, Calif. 94520.

At block 106, 2-D scans of the selected specimen are taken. In one embodiment, the scans of the selected sample specimen are taken using a Micro CT scanner. In another embodiment, the scans of the sample selected specimen are taken using a Nano CT scanner. For example, Micro CT scanning has sufficient resolution to image sample specimens such as sandstones, oil sands, most carbonates and tight gas sandstones and the like. However, some carbonates, tight gas and shale formations require imaging at much higher resolutions. Shales have some of the smallest pores found in any elastic or nonelastic reservoir rock. Hydrocarbon flow in shale reservoirs occurs in pore structures that are orders of magnitude smaller than typical sandstone or carbonate reservoirs. In an embodiment, a Nano CT scanner may have a resolution of at least 0.05 microns. In another embodiment, a special Micro CT scanner may be used for drill cuttings.

CT scan imaging of a porous sample specimen is used in the invention to produce a numerical object that represents the material sample digitally in the computer for subsequent numerical simulations of various physical processes. The CT scan image produced by the CT scanner may be a 3D numerical object consisting of a plurality of 2D sections of the imaged sample. Each 2D section consists of a grid of values each corresponding to a small region of space defined within the plane of the grid. Each such small region of space is referred to as a "pixel" and has assigned thereto a number representing the image darkness (or for example the density of the material) determined by the CT scan procedure. The value ascribed to each pixel of the 2D sections is typically an integer that may vary between zero and 255 where 0 is, e.g., pure white, and 255 is pure black. Such integer is typically referred to as a "gray scale" value. The 0 to 255 integer is associated with eight digital bits in a digital word representing the gray scale value in each pixel. Other gray scale ranges may be associated with longer or shorter digital words in other implementations, and the range of 0 to 255 is not intended to limit the scope of the invention.

For the purpose of simulating a physical process using such a numerical object (the gray scale), however, the numerical object is preferably processed so that all the pixels allocated to the void space in the rock formation (pore space) are represented by a common numerical value, e.g., by only 255s, and all the pixels associated with the rock matrix (or rock grains) are represented by a different numerical value, for example, zeroes. The foregoing process is called image segmentation at block 108. Subsequently, the resulting numerical object can be normalized so that the pore spaces are represented by, for example, ones and the rock grains are represented by other examples, the image may be converted into an index having any selected number, n, of indices. It has been determined that sufficiently accurate modeling of rock properties may be obtained using a binary index, in which one value represents pore space and another single value represents rock grains.

A technique known in the art for segmenting a gray-scale object is called "thresholding," where all pixels having a gray scale value below a selected threshold value are identified as grains, while all other pixels are identified as pore space. The foregoing approach is often not satisfactory, however, because due to numerical clutter in an unprocessed CT scan image, some pixels physically located inside a grain may have the gray level of the pore space and vice versa. In the invention, a type of image segmentation known as "region growing" may be used. Region growing may be described as follows. Consider a 2D section of a CT scan image made of a porous rock formation. A substantial number of "seeds" is placed within the image. All pixels within a seed are assigned the same gray scale level which may be an average (e.g., arithmetic) of the gray levels of all the pixels within the seed. The seeds in the image frame do not overlap spatially. Next, two or more adjacent seeds are merged and are identified as a "region" if the gray scale levels of the adjacent seeds have gray scale values within a selected difference threshold of each other. Each identified region is assigned a uniform (fixed) gray level, which can be a weighted average of the gray scale values of all the seeds that have been merged into the identified region. The foregoing process continues for all regions thus formed in the image frame. As a result, the unprocessed CT image is transformed into internally uniform regions plus unclassified pixels that were not assigned to any of the identified regions (because such pixels included gray scale values outside the allocation threshold criteria). Each of such unclassified pixels can be assigned to an adjacent region with the closest gray scale level. If the resulting number of regions is greater than two, however, the foregoing method simply fails to allocate the CT image correctly into grains and pores.

To address the foregoing problem with extending ("growing") seeds into regions, in the invention, instead of using seeds having different gray scale values, only two classes of seeds are used: all pixels having a gray scale value below a selected initial limit for the gray scale level of rock grains are classified as rock grains; and all pixels in which the gray scale level is larger than a selected initial limit for pore spaces are classified as pore space. One simple way of specifying these initial limits is by selecting the gray scale levels corresponding to the peaks of a gray level histogram. In many subsurface formations, such a histogram will be bimodal, wherein one mode value will correspond to the gray scale level of pores, and another mode value will correspond to the gray scale level of rock grains.

The next element in image classification according to the invention is to grow each of the two initially formed seeds by allocating to such seeds all adjacent pixels having gray scale levels within a selected tolerance. The foregoing process can continue by incrementally increasing the gray scale lower limit for rock grains and incrementally reducing the gray scale upper limit for pore spaces until the two limits meet. The result is that all pixels will be allocated to either pore space or to rock grains, thus providing a fully segmented image.

One possible advantage of the foregoing procedure is that instead of forming multiple regions, the foregoing technique grows only two distinctive regions from start to end, thus avoiding the situation where multiple distinctive regions appear and then have to be reclassified into either pores or grains. If the resulting segmented image appears noisy (cluttered), it can be smoothed by any one of conventional filters.

The procedure is illustrated by the following steps.

Step 1. Preprocessing of raw image. Preprocess the original image using the median or 2D gaussian kernel filter. The size of the filter is provided by the user and should depend on, among other factors, the quality of the image (level of noise). It should be noted that the image segmenting procedure that follows has been demonstrated to be sufficiently noise resistant as to make the preprocessing frequently unnecessary.

Step 2. Initializing seeds. Two user-selected thresholds, $t_1$ and $t_2$, are selected to determine initial regions for pore space and rock grains, respectively. The initial thresholds may be selected, for example, by analysis of a histogram of the gray scale values in the CT image. For every pixel $p_i$ having a gray scale level represented by $B(p_i)$:

if $B(p_i) > t_1$ then $p_i$ is identified as pore space; and
if $B(p_i) < t_2$ then $p_i$ is identified as grain.

If there are two or more contiguous pixels in any subset of the image frame that are classified according to the threshold procedure above, such contiguous pixels may be referred to as "clusters." All of the pixels allocated as explained above then become the image seeds from which region growing proceeds.

Step 3. Region growing. For each pixel classified as a pore, its eight neighbors (spatially contiguous pixels) in the 2D image plane are interrogated. If any of the interrogated neighbor pixels is not already identified as pore or rock grain, and the gray scale level of such pixel is within a preselected tolerance level of (or initially selected different between) the gray scale level assigned to the "pore" seed (as in Step 2 above), the interrogated neighbor pixel is then classified as a pore and is allocated to the "pore" cluster.

The foregoing contiguous pixel interrogation is also performed for pixels classified as rock grain. Contiguous, previously unallocated pixels having gray scale level within a preselected tolerance of the gray scale level of the rock grain seed are allocated to the rock grain cluster.

The foregoing cluster allocation and region growing process continues for both pore space and rock grain until all the pixels in the 2D image frame are interrogated. If any of the pixels is not classified as pore space or rock grain, the foregoing tolerance value for each of the pore space and the rock grain may be increased by a selected increment, and the contiguous pixel interrogation and classification may be repeated. The foregoing tolerance increase and repeated adjacent pixel interrogation may be repeated until all or substantially all the pixels in the 2D image frame are allocated to either rock grain or pore space.

The foregoing region growing procedure is then repeated for each 2D image frame in the 3D CT scan image. The result is a three-dimensional characterization of the pore structure of the rock samples on which CT imaging has been performed.

Figure 2:
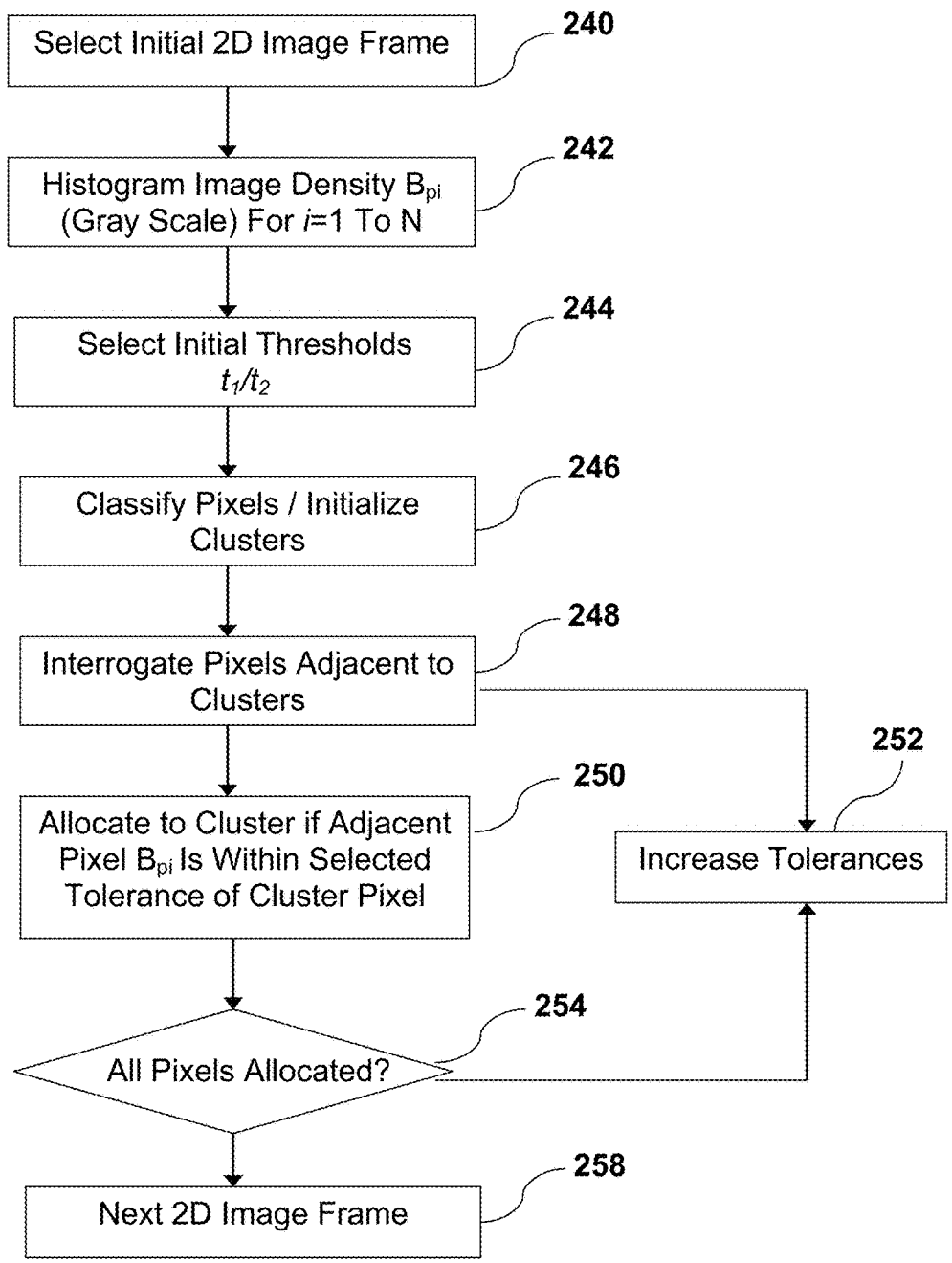
FIG. 2 is a flow chart of an example process including CT image analysis.

FIG. 2 is an example implementation of the above process for image segmentation from block 108. At 240, a 2D image frame of a CT scan image is selected. The image frame may be subjected to histogram analysis, at 242 to determine possible mode values of gray scale for pore spaces and for rock grains. At 244, the possible modes of the histogram may be used to set initial values for the image segmentation thresholds $t_1$ and $t_2$. At 246, using the initial segmentation thresholds, all pixels in the image frame are allocated to pore space or to rock grains, depending on whether the gray scale value in each pixel exceeds the respective segmentation threshold. The allocated pixels are then segmented into seeds where two or more contiguous pixels are allocated to either pore space or rock grain. At 248, pixels adjacent to the each of the seeds are interrogated. Previously unallocated pixels having a gray scale value falling within an initially selected threshold difference (or tolerance) of the adjacent cluster pixel gray scale value are allocated to the seed at 250. At 254, the image frame is interrogated to determine if all or substantially all the image frame pixels have been allocated to either pore space or rock grain. At 254, the number of allocated pixels is counted and if all or substantially all the pixels in the image frame have been allocated, a new 2D image frame can be selected, at 258, and the above process repeated. Typically the next 2D image frame will be adjacent to the most recently analyzed 2D image frame. The above process can be repeated until all available 2D image frames have been analyzed. If all pixels in the image frame have not been allocated, at 252, the tolerance or difference threshold values used at 250 may be increased and the interrogation of pixels adjacent to the existing seeds can be repeated, at 248, and the remainder of the process can be repeated.

This process results in a digital version of the actual fabric of the original physical rock, a 3-dimensional digital model 110 referred to as a vRock™. The vRock™ of the sample rock specimen provides a complete pore network at a level of detail that permits the calculation of physical and fluid flow properties of the porous media.

At block 112, physical and fluid flow properties are computed for the selected sample specimen using the pore space geometry and grain structure provided in the vRock™. The vRock™ is used in an embodiment to compute the porosity as the ratio of the number of voxels that fall into the segmented pore space to the total number of voxels in a 3-D image. Both effective porosity and isolated porosity are provided.

In one embodiment, the vRock™ of the selected sample specimen is used to determine an absolute permeability. To determine absolute permeability, a pressure head or body force is directly applied to the vRock™. The resulting fluid flux is then computed and permeability is calculated according to Darcy's equation. The calculation is performed by simulating fluid flow through the vRock™. In accordance with the invention, the calculation of a physical property of the selected sample specimen, such as the determination of absolute permeability, does not exclude the calculation of another physical property of the same selected sample specimen.

In accordance with the invention, the determination of physical properties of the selected sample specimen is performed such that the sample specimen remains intact. In particular, the selected sample specimen remains intact to the extent that the selected sample specimen is not destroyed in the process of calculating physical properties. Although some change in composition of the selected sample specimen may be performed in preparing the selected sample specimen, in whole, the selected sample specimen remains intact for another use or scan.

The vRock™ of the selected sample specimen may also be used to determine another physical property, such as electrical conductivity. To determine electrical conductivity, the Laplace equation is solved in the conductive pore space, which is digitally completely saturated with brine, by means of the finite element method (FEM). The electrical current field in the pores is computed and then summed-up to obtain the total current through the selected sample specimen. The effective conductivity of the selected sample specimen is the ratio of this current to the potential drop per unit length, and the formation factor is the ratio of brine conductivity to the conductivity of the sample. The method directly accounts for conductive components of the mineral matrix, such as pyrite or conductive clay, by assigning appropriate specific conductivity to these components.

The physical property of electrical conductivity may be determined using the same selected sample specimen that is used to measure another physical property, such as absolute permeability. By using the same selected sample specimen to determine multiple physical properties, the results are more consistent than using multiple specimens to obtain physical properties for a particular reservoir. The present example is not meant to limit the types of consistent set of physical properties that can be obtained using the same sample specimen, but rather to illustrate that multiple physical properties may be obtained from the same selected sample specimen by using the vRock™ of the specimen.

The vRock™ of the selected sample specimen may also be used to determine elastic properties. To determine elastic properties, a static deformation experiment is simulated on a vRock™. The application of stresses to the faces of the sample generates strains in the rock frame that are computed locally using the finite element method (FEM). The resulting effective deformations of the sample are related to the stresses applied at the boundaries to calculate the effective elastic moduli. This application assumes linear elasticity laws are valid within the sample selected specimen. The elastic moduli thus obtained can be converted into the elastic-wave velocities. Elastic moduli define the properties of material that undergoes stress, deforms, and then recovers and returns to its original shape after the stress ceases. The elastic moduli include the bulk modulus, Lame constant, Poisson's ratio, shear modulus, and Young's modulus. These physical properties may also be obtained using the same selected sample specimen by using the 3-dimensional digital model of the sample specimen, leaving the selected sample specimen intact. Compressibility, the ratio of the percent change in volume to the change in pressure applied to a fluid or rock, may also be measured in accordance with the present invention.

The vRock™ of the selected sample specimen may also be used to determine relative permeability. Relative permeability is the ratio of effective permeability of a particular fluid at a particular saturation to the absolute permeability of that fluid at total saturation. The slow multiphase viscous flow for estimating relative permeability is simulated using the Lattice Boltzmann method (LBM). The LBM mathematically mimics the equations of multiphase viscous flow by treating the fluid as a set of particles with interaction rules between the particles belonging to the same fluid, different fluids, and the fluids and pore walls. The LBM directly simulates static and dynamic configurations of the contacts between the fluid phases and the pore walls by taking into account surface tension and contact angles. It allows for the estimation of irreducible water and hydrocarbon saturations.

The present invention may also measure the physical properties of sample porous media such as regular core material or rock fragments unsuitable for a conventional physical laboratory, such as sidewall cores and drill cuttings. The ability to determine properties of rock fragments in accordance with the present invention is regarded due to the difficulty of extracting core from deviated wells and because it is currently not possible to extract from slimhole wells.

The physical properties obtained in accordance with the method above yield a consistent set of parameters, such as, permeability, formation factor and relative permeability in an example set, from the same sample specimen for use in reservoir modeling. These physical properties may be used in numerical or reservoir simulators to yield solutions in these simulators that are more consistent because they are obtained from the same sample specimen, come to stabilization sooner in the simulator, and require less history matching overall. Other information in addition to the physical properties of porous media of a reservoir is needed to fully characterize oil and gas reservoirs for evaluation purposes. In one embodiment, the results obtained in accordance with the present invention regarding physical properties may be used in combination with other reservoir information to determine where to drill wells, how to complete wells, how efficiently wells are producing, and when the wells are depleted. The quality of the input data is critical to achieving a result that has a high probability of being consistent and accurate in reservoir modeling.

Figure 3A:
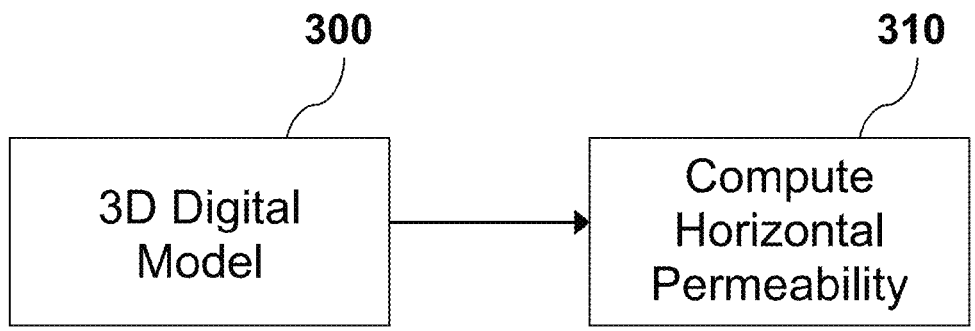
FIG. 3A is a flow chart illustrating the calculation of a physical property, horizontal permeability, using the present invention.

FIG. 3A is a flow chart illustrating the calculation of the physical property of horizontal permeability using the present invention. In 300, a 3-D digital model of the selected sample specimen, the vRock™ may be used to determine a physical property. At 310, the vRock™ of the selected sample specimen is used to calculate the horizontal permeability. To calculate horizontal permeability, a simulation is performed on vRock™ and the vRock™ is cut parallel to the core's axis to receive a fluid flow. The result is measured on the vRock™ to obtain the horizontal permeability.

Figure 3B:
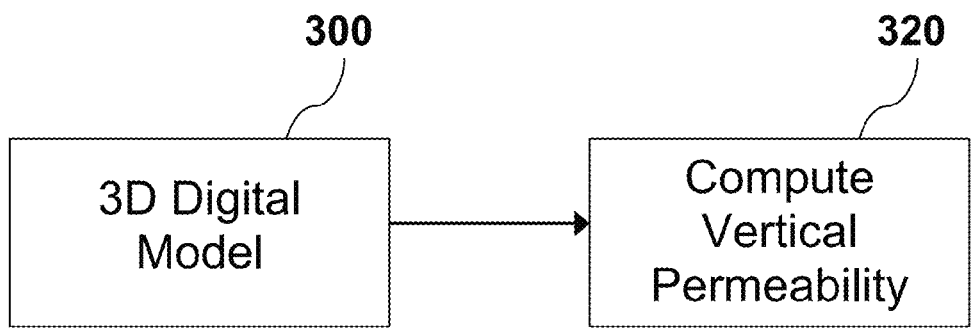
FIG. 3B is a flow chart illustrating the calculation of a physical property, vertical permeability, using the present invention.

FIG. 3B is a flow chart illustrating the calculation of the physical property of vertical permeability using the present invention. In 300, a 3-D digital model of the selected sample specimen, the vRock™ may be used to determine a physical property. At 320, the vRock™ of the selected sample specimen is used to calculate the vertical permeability. To calculate vertical permeability, a simulation is performed on vRock™ and the vRock™ is cut perpendicular to the core's axis to receive a fluid flow. The result is measured on the vRock™ to obtain the vertical permeability. In accordance with the present invention, the selected sample specimen remains intact as the fluid flow required to calculate the horizontal or vertical permeabilities is conducted through the digital representation, vRock™ of the selected sample specimen. Any or all of the foregoing estimated physical properties may be stored and/or displayed in the computer.

FIG. 4A-4C show one of the selected sample specimens examined in accordance with the present invention.

FIG. 4A is a chair display of the raw 3-D volume generated in accordance with the process of FIG. 1.

FIG. 4B shows 3 axial slices of FIG. 3A, the raw 3-D volume.

FIG. 4C is a single 2-D slice of the segmented image. In one embodiment, the segmentation process may result in an image that can identify the bitumen 430, quartz grains 432, and pore space 434 based on variations in density.

An example of a beneficial use of this invention is in populating reservoir simulators with data obtained from the 3-D digital model. Reservoir simulators sometimes require millions of input data sets that must be consistent with the geological environment and petroleum system. Inaccuracies in some data will necessarily produce output with compensatory inaccuracies in other areas. Another use of improved data consistency is in performing nodal analysis on individual wells to predict and evaluate production rates. Consistent and accurate knowledge of relative permeability requires, among other things, detailed knowledge of the amount and geometry of the pore space in the rock and how much water is present. Depending on the rock type, relative permeability values might be more or less dependant on flow rate. Completion design techniques can also be improved with consistent data from the 3-D digital model because of higher confidence in the accuracy of the data. For example, accurate knowledge of the ratio of horizontal to vertical permeability can be used to determine where to perforate a well with a known water contact. Other benefits of having consistent data sets will be apparent to those skilled in the art.

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered or modified and all such variations are considered within the scope and spirit of the present invention. While compositions and methods are described in terms of "comprising," "containing," or "including" various components or steps, the compositions and methods can also "consist essentially of" or "consist of" the various components and steps. All numbers and ranges disclosed above may vary by some amount. Also, the terms in the claims have their plain, ordinary meaning unless otherwise explicitly and clearly defined by the patentee. Moreover, the indefinite articles "a" or "an", as used in the claims, are defined herein to mean one or more than one of the element that it introduces. Also, the terms in the claims have their plain, ordinary meaning unless otherwise explicitly and clearly defined by the patentee. If there is any conflict in the usages of a word or term in this specification and one or more patent or other documents that may be incorporated herein by reference, the definitions that are consistent with this specification should be adopted.

What is claimed is:

1. A method of obtaining consistent and integrated physical properties of a porous specimen for modeling a reservoir, comprising:
receiving an unprepared sample specimen of porous media, wherein the unprepared sample specimen was extracted from the Earth, and the unprepared sample specimen is a whole core section or a core plug;
preparing the unprepared sample specimen for imaging, wherein the preparing results in a single sample specimen for use in obtaining parameters for reservoir modeling, wherein the preparing comprises:
determining whether to remove a portion of the unprepared sample specimen,
wherein if it is determined that the portion of the unprepared sample specimen should be removed, removing the portion of the unprepared sample specimen that is representative of a core of the unprepared sample specimen resulting in the single sample specimen,
and if it is determined that the portion of the unprepared sample specimen should not be removed, the unprepared sample specimen is used as the single sample specimen,
imaging the single sample specimen to generate a three-dimensional tomographic image of the sample specimen;
segmenting the image into pixels, each pixel representing a pore space or a grain;
wherein the segmenting renders a three-dimensional digital model of the single sample specimen;
performing, using a computer, a set of computations based on the three-dimensional digital model of the single sample specimen,
wherein the set of computations determines a plurality of physical properties of the single sample specimen,
and wherein the single sample specimen is not destroyed in said method and remains intact throughout the method.

2. The method of claim 1 further comprising utilizing the plurality of physical properties to model a reservoir.

3. The method of claim 1 further comprising utilizing the plurality of physical properties to determine oil and gas reserves.

4. The method of claim 1 further comprising utilizing the plurality of physical properties to perform a nodal analysis.

5. The method of claim 1 further comprising utilizing the plurality of physical properties to design well completions.

6. The method of claim 5, wherein the well completions involves selecting a perforated interval.

7. The method of claim 5, wherein the well completions further includes a sand control system.

8. The method of claim 5, wherein the well completions further includes selecting a production tubing size.

9. The method of claim 1, wherein the plurality of physical properties comprise rock properties.

10. The method of claim 1, wherein the plurality of physical properties comprise two or more of porosity, absolute permeability, horizontal permeability, vertical permeability, electrical conductivity, elastic properties, or relative permeability.

11. The method of claim 1 wherein the segmenting comprises:
(a) determining an initial gray scale threshold for each of pore space and rock grain;

(b) allocating each pixel in the image to a pore space seed or rock grain seed for each pixel meeting threshold criteria for each of the pore space and rock grain thresholds, respectively;

(c) interrogating pixels adjacent to each pore space seed and rock grain seed;

(d) allocating the interrogated adjacent pixels previously not allocated to a seed to the pore space seed or the rock grain seed based on threshold criteria; and (e) repeating (c) and (d) until pixels in the image are allocated to the rock grain or the pore space.

12. The method of claim 11 wherein the determining of the initial gray scale threshold comprises histogram analysis of the tomographic image.

13. The method of claim 11 wherein the allocating interrogated adjacent pixels comprises determining a difference between a gray scale value assigned to said pore space seed or rock grain seed and a gray scale value of the pixels adjacent to each pore space seed and rock grain seed, and allocating the interrogated pixel to the seed if the difference falls below a selected difference threshold.

14. The method of claim 1, wherein the preparing further comprises determining to remove a portion of the unprepared sample specimen, wherein the unprepared sample specimen is a whole core and the portion is a core plug which is representative of the core, and removing the core plug as the single sample specimen.

15. The method of claim 1, wherein the preparing the single sample specimen further comprises choosing a subsample of the sample specimen for imaging.

16. A system for obtaining consistent and integrated physical properties of a porous specimen for modeling a reservoir, the system comprising:

a means for preparing an unprepared sample specimen of porous media, wherein the unprepared sample specimen was extracted from the Earth and collected, and the unprepared sample specimen is a whole core section or a core plug, and further wherein the unprepared sample specimen is prepared for imaging, wherein the preparing results in a single sample specimen for use in obtaining parameters for reservoir modeling, wherein the preparing comprises:

determining whether to remove a portion of the unprepared single sample specimen, wherein if it is determined that the portion of the unprepared sample specimen should be removed, removing the portion of the unprepared sample specimen that is representative of a core of the unprepared sample specimen resulting in the single sample specimen, and if it is determined that the portion of the unprepared sample specimen should not be removed, the unprepared sample specimen is used as the single sample specimen, a CT scanner for obtaining a three-dimensional tomographic image, wherein the three-dimensional tomographic image is obtained by imaging the single sample specimen with the CT scanner, and wherein the three-dimensional tomographic image is segmented into pixels, each pixel representing a pore space or a grain, to render a three-dimensional digital model of the single sample specimen; and a computer, wherein the three-dimensional digital model is used to perform a set of computations with the computer for obtaining a plurality of physical properties of the single sample specimen, wherein the single sample specimen is not destroyed in said method and remains intact throughout.

17. A method of obtaining consistent and integrated physical properties of a porous specimen for modeling a reservoir, comprising:

receiving an unprepared sample specimen of porous media, wherein the unprepared sample specimen was extracted from the Earth, and the unprepared sample specimen is a whole core section or core plug thereof;

preparing the unprepared sample specimen for imaging, wherein the preparing results in a single sample specimen for use in obtaining parameters for reservoir modeling, wherein the preparing comprises:

determining whether to remove a portion of the unprepared sample specimen, wherein if it is determined that the portion of the unprepared sample specimen should be removed, removing the portion of the unprepared sample specimen that is representative of a core of the unprepared sample specimen resulting in the single sample specimen, and if it is determined that the portion of the unprepared sample specimen should not be removed, the unprepared sample specimen is used as the single sample specimen, imaging the single sample specimen to generate a three-dimensional tomographic image of the sample specimen;

segmenting the image into pixels, each pixel representing a pore space or a grain, wherein the segmenting renders a three-dimensional digital model of the single sample specimen;

performing, using a computer, a set of computations based on the three-dimensional digital model of the single sample specimen, wherein the set of computations determines one or more physical properties of the single sample specimen in a horizontal direction and in a vertical direction, and wherein the single sample specimen remains intact throughout the method.

18. The method of claim 17, wherein said one or more physical properties in a horizontal direction comprise a horizontal permeability and said one or more physical properties in a vertical direction comprise a vertical permeability.

19. The method of claim 18, further comprising determining a ratio of the horizontal permeability and the vertical permeability, and determining where to perforate a well with a known water content using said ratio.

20. The method of claim 17, further comprising determining a ratio between one or more physical properties in the horizontal direction and one or more physical properties in the vertical direction.

* * * * *